United States Patent [19]
Thayer et al.

[11] Patent Number: 5,281,409
[45] Date of Patent: Jan. 25, 1994

[54] LOW-MISTING ANTIPERSPIRANT AEROSOL COMPOSITIONS

[75] Inventors: Bianca K. Thayer, Greenwich; Raymond J. Thimineur, Scotia, both of N.Y.

[73] Assignee: General Electric Company, Waterford, N.Y.

[21] Appl. No.: 944,807

[22] Filed: Sep. 14, 1992

Related U.S. Application Data

[63] Continuation of Ser. No. 510,913, Apr. 18, 1990, abandoned.

[51] Int. Cl.$^5$ .............................. A61K 7/32; A61K 7; A61K 34; A61K 7/38; A61K 9/12
[52] U.S. Cl. ........................................ 424/47; 424/66; 424/68
[58] Field of Search ...................... 424/45, 46, 47, 66, 424/68

[56] References Cited

U.S. PATENT DOCUMENTS

| | | | |
|---|---|---|---|
| 2,872,379 | 2/1959 | Neumann et al. | 424/47 |
| 3,088,874 | 5/1963 | Geary et al. | 424/47 |
| 3,798,317 | 3/1974 | Gorum | 424/47 |
| 4,152,416 | 5/1979 | Spitzer et al. | 424/46 |
| 4,174,386 | 11/1979 | Spitzer et al. | 424/46 |
| 4,806,338 | 2/1989 | Smith | 424/47 |

FOREIGN PATENT DOCUMENTS 0343843 5/1989 European Pat. Off. .............. 424/47

Primary Examiner—Dale R. Ore

[57] ABSTRACT

An aerosol antiperspirant composition capable of being dispensed from aerosol containers with reduced mistiness and dustiness is provided, which comprises by weight:

(A) from about 0.1 to about 5.0% of a compound comprising by weight (1) from about 60% to about 95% of a silicone gum and (2) about 5% to about 20% of an untreated reinforcing silica filler or about 5% to about 40% of a treated reinforcing silica filler;

(B) from about 3% to about 20% of a diluent fluid selected from a volatile silicone or organic fluid and a mixture of a volatile silicone fluid and a nonvolatile organic or silicone fluid;

(C) an antiperspirant salt in an amount within the range from about 2 to about 20%; and (D) a liquefied propellant in an amount within the range from about 50% to about 90%.

Preferably, the composition further comprises about 0.1% to about 3% of a bulking agent and about 0.1% to about 3% of a polar organic solvent.

31 Claims, No Drawings

LOW-MISTING ANTIPERSPIRANT AEROSOL COMPOSITIONS

This is a continuation of copending application Ser. No. 07/510,913 filed on Apr. 18, 1990 now abandoned.

BACKGROUND OF THE INVENTION

The present invention relates to powdered aerosol compositions. More particularly, this invention relates to powdered aerosol compositions having improved application characteristics.

Aerosol sprays are now widely used, particularly in the cosmetic, topical pharmaceutical and detergent fields, for delivery of an additive such as a cosmetic, pharmaceutical, or cleaning composition to a substrate such as the skin or other surface to be treated. Aerosol compositions are widely used as antiperspirants to direct the antiperspirant to the skin in the form of a finely divided spray.

Aerosol antiperspirant compositions typically are anhydrous systems comprising an antiperspirant salt dispersed in a liquid vehicle together with a liquefied volatile propellant in a pressurized aerosol container. The aerosol spray is created by the rapid boiling of the propellant upon dispensing from an atomizing valve. Such aerosol containers are described, for example, in U.S. Pat. Nos. 3,083,917, 3,083,918 and 3,544,258.

Fine sprays dispersed from a container containing a powdered aerosol composition can give rise to stable aerosols of finely divided liquid particles, referred to as mistiness, and further can produce a fine dust of suspended solids which settles only slowly, referred to as dustiness. A drawback associated with aerosol compositions is that they can create excessive dustiness or mistiness during application.

Excessive mistiness and dustiness of an aerosol composition can lead to waste in that less of the composition reaches its intended target, and, further, can result in an increase in airbourne particles which has a deletorious effect on the environment and makes breathing near the application site more difficult.

Attempts have been made in the art to produce aerosol antiperspirant compositions having reduced mistiness and dustiness upon application. For example, U.S. Pat. No. 4,806,338 to Smith discloses an aerosol antiperspirant composition purportedly having improved application, cosmetic and performance characteristics, wherein the composition contains a particulate antiperspirant, a functionalized siloxane, an aerosol propellant, and optionally a silicone gum, a volatile silicone oil, and a bulking agent.

U.S. Pat. No. 4,152,416 to Spitzer et al. (Spitzer) disclose an aerosol antiperspirant composition reported to be capable of being dispensed from aerosol containers with low mistiness and dustiness. The Spitzer composition contains an antiperspirant salt, a liquefied propellant, a bulking agent a synthetic polymer gum which may be a silicone gum, and optionally a nonvolatile liquid such as isopropyl myristate.

Although powdered aerosol compositions having good application characteristics are known in the art, it is continually desired to provide powdered aerosol compositions having improved application properties.

It is further desirable to provide powdered aerosol compositions having reduced mistiness and dustiness upon dispensation from an aerosol container.

SUMMARY OF THE INVENTION

The present invention provides an aerosol antiperspirant composition capable of being dispensed from an aerosol container with low mistiness and dustiness, comprising by weight:

(A) from about 0.1 to about 5.0% of a compound comprising by weight (1) from about 60% to about 95% of a silicone gum and (2) about 5% to about 20% of an untreated reinforcing silica filler or about 5% to about 40%. of a treated reinforcing silica filler;

(B) from about 3% to about 20% of a diluent fluid selected from a volatile silicone or organic fluid and a mixture of a volatile silicone or organic fluid and a non-volatile organic or silicone fluid;

(C) an antiperspirant salt in an amount within the range from about 2 to about 20%; and (D) a liquefied propellant in an amount within the range from about 50% to about 90%.

The present invention is further directed to a method for preparing the composition set forth above and to a method for reducing the mistiness and dustiness of an antiperspirant composition.

The present invention is based on the discovery that the presence of a reinforcing silica-filled silicone gum compound in an aerosol antiperspirant composition will result in reduced mistiness and dustiness upon the dispensation of the composition from an aerosol container.

DETAILED DESCRIPTION OF THE INVENTION

Although the invention will be described hereinafter with reference to antiperspirant aerosol compositions, it is to be understood that the invention is also applicable to other powdered aerosol systems.

In one aspect, the present invention is directed to an aerosol antiperspirant composition containing a compound of silicone gum and reinforcing silica filler. The silicone gum/reinforcing silica filler compound will sometimes be referred to herein as "reinforced silicone gum" or "reinforced gum."

As mentioned previously herein, the presence of the reinforced silicone gum in the antiperspirant aerosol composition reduces the misting and dusting of the aerosol composition upon its dispensation from an aerosol container and further acts as a suspension aid in the suspension of powdered solids in an aerosol system.

Ultra centrifuge testing revealed that once the reinforced silicone gum is dispersed in the volatile silicone fluid, the reinforced gum does not separate back into gum and filler. The reinforced gum remains a compound, with actual particle size measurement capability, much like an emulsion or dispersion. Although nct wishing to be bound to any theory, it is believed that the mechanism of mist and dust reduction is a result of the cohesive forces resulting from the hydrogen bonding between the reinforced silicone gum and the reinforcing silica filler, and the hydrogen bonding between the filler in the reinforced gum and the remaining components of the composition. The presence of the filler in the silicone gum causes the reinforced gum particles to act as nucleating sites, attracting other gum particles and particles of the other components in the composition, resulting in less mistiness and dustiness. These cohesive forces can also aid in the suspension of aerosol powders. The result i s a wetter, coarser spray with less misting.

The reinforced silicone gum of component A is used in the composition and methods of this invention in an amount within the range from about 0.1% to about 5.0%, and preferably about 0.5% to about 1.5% by weight of the composition.

The reinforced silicone gum comprises by weight from about 5% to about 40% and preferably from about 15% to about 30% of the reinforcing silica filler.

The reinforced silicone gum is prepared by blending the silicone gum and the reinforcing filler together until the filler is completely and uniformly dispersed throughout the composition to form a homogeneous material.

The filler should be dispersed throughout the gum mixture as it is added so that it does not form lumps of high filler content, which are then difficult to break up and disperse in the rest of the compound.

The reinforced gum can be prepared by using conventional blending techniques. Methods of mixing that are common in the silicone rubber art and which are suitable for this invention include mixing with a dough mixer, a rubber compounding mill, or with a Banbury mixer.

As referred to herein, "silicone gum" materials useful in the composition of this invention are organopolysiloxanes having a viscosity of from about 500,000 to about 100,000,000 centistokes at 25° C. Silicone gum suitable for use in this invention include those having the following general formula:

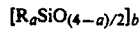
$$[R_aSiO_{(4-a)/2}]_b$$

in which R independently represents an unsubstituted or substituted monovalent hydrocarbon radicals having 1 to about 10 carbon atoms, preferably 1 to about 8 carbon atoms, such as, for example, an alkyl group, e.g., methyl, ethyl, propyl, butyl, and the like; an alkenyl group, e.g., vinyl, allyl, butenyl, and the like; an aryl group, e.g., phenyl, tolyl, xylyl, styrene, and halogenated derivatives of the above radicals, including chloromethyl, chlorophenyls and the like.

In formula (I) above, "a" is a number of from 0 to about 3, and "b" is a number from about 2000 to about 15,000, preferably 2000–7000.

The organopolysiloxane is preferably a linear or branched polydimethylsiloxane which can be blocked with terminal hydroxyl groups, triorganosilyl groups, diorganovinylsilyl groups, organodivinylsilyl groups, or trivinylsilyl groups.

The most preferred silicone gums are linear polydimethylsiloxanes blocked with either terminal dimethylvinylsilyl groups or with terminal trimethylsilyl groups.

Silicone gums among those useful herein are available from a variety of commercial sources and include SE76, SE30, SE73, SE63, and SE32 Silicone Gums (manufactured by General Electric Company).

Reinforcing silica fillers useful in this invention have a surface area of from 50 to greater than 400 m²/g. These reinforcing silica fillers are well known in the art and can be obtained commercially. Examples of suitable reinforcing silica filler include fumed silica and precipitated silica. The most preferred reinforcing silica filler for use in the present invention is fumed silica.

The preferred fillers for use in the composition and methods of this invention are "treated" reinforcing silica fillers wherein the fillers have been surface treated so as to render them essentially hydrophobic. Treated fillers are preferred because they tend to prevent or hinder interaction between the polydiorganosiloxane and the filler that may increase the viscosity of the composition to the extent that it becomes unprocessable. The term "untreated" reinforcing filler or "untreated" filler refers to a reinforcing filler which has not been treated to render it essentially hydrophobic.

Methods for surface treating reinforcing silica fillers so as to render the fillers essentially hydrophobic are known in the art. The fumed silica or precipitated silica may be treated with cyclic organopolysiloxanes under heat and pressure as taught in U.S. Pat. No. 2,938,009 to Lucas or in U.S. Pat. No. 3,334,062 to Brown, both of which are herein incorporated by reference. Alternatively, the fumed silica or precipitated silica may be exposed to siloxanes or silanes in the presence of an amine compound, as taught in U.S. Pat. No. 3,024,126, which is herein incorporated by reference. The fumed silica or precipitated silica may be treated with ammonia or a silazane as taught in U.S. Pat. No. 3,635,743 to Smith or in U.S. Pat. No. 3,847,848 to Beers, both of which are herein incorporated by reference.

The amount of reinforcing silica filler used in the present invention is dependent upon whether treated or untreated fillers are used. If an untreated filler is used, it is generally present in an amount within the range of about 5 to about 20%, preferably about 10 to about 15% by weight of the total weight of the composition. When a treated reinforcing filler is used, it is typically used in an amount within the range of about 5 to about 40%, preferably about 15 to about 30%, by weight of the total composition. Lower amounts of the untreated filler are used because an excess amount can lead to an increase in the viscosity of the silicone gum, rendering the gum unprocessable.

Component B of the composition of this invention is a diluent fluid selected from a volatile silicone or organic fluid and a mixture of a volatile silicone or organic fluid and a non-volatile organic or silicone fluid. The diluent liquid is used in the composition and methods of this invention in an amount within the range from about 3% to about 20% and preferably about 6% to about 15% by weight of the composition.

As used herein, "volatile" refers to those materials which have a measurable vapor pressure at ambient conditions.

Suitable volatile silicone fluids may be cyclic or linear. A description of various volatile silicone oils is found in Todd, et al., "Volatile Silicone Fluids for Cosmetics", 91 Cosmetics and Toiletries, 27–32 (1976), incorporated by reference herein. Linear volatile silicones generally have viscosities of less than about five centistokes at 250° C., whereas the cyclic silicones have viscosities of less than about 10 centistokes.

In general, the volatile silicone fluid can be any combination of tetramer, pentamer, and hexamer, or a low viscosity diorgano fluid. Generally, suitable cyclic volatile silicone fluids can be represented by the formula:

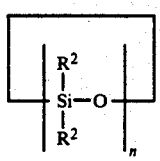

wherein $R^2$ is a 1 to 3 carbon alkyl group and n is a number from 3 to 10, preferably from 3 to 7.

Examples of volatile silicone fluids useful in the present invention include, for example, (a) (i) SF 1202, containing a pentamer in a minimum amount of 95%, and 5% of other cyclics; (ii) SF 1204, containing 85% of pentamer and 15% of tetramer; (iii) SF 1173, containing 95% of tetramer and 5% of other cyclics; all of the foregoing products being available from General Electric Company; (b) Dow Corning 344 fluid, wherein $R^2$ is methyl and wherein the fluid typically comprises by weight about 88% tetramer, about 11.8% pentamer, and traces of trimer and hexamer; and (c) SWS-03314 (sold by SWS Silicones, a Division of Stauffer Chemical Company) in which $R^2$ is methyl and which is substantially all tetramer.

The preferred volatile silicone fluids for use in this invention are the cyclomethicone pentamer and the cyclomethicone tetramer. The most preferred volatile silicone fluid is the cyclomethicone pentamer.

Examples of suitable volatile organic fluids are linear or branched isoparaffinic hydrocarbons having about 6 to about 16 carbon atoms and preferably about 10 to about 14 carbon atoms. The most preferred isoparaffinic hydrocarbons are those available from Exxon Corporation and having the designation ISOPAR (Registered Trade Mark).

The term "nonvolatile" means that the liquid will not volatilize during the time the composition is on the skin and before it is absorbed. This usually requires only a few minutes. Thus, the term "nonvolatile" does not exclude materials that are slowly volatile and require a long time to evaporate fully, such as the low viscosity linear silicones. These are generally polydimethylsiloxanes of low viscosity, e.g., about 3 to 10 centistokes at 25° C.

Nonvolatile organic liquids such as isopropyl myristate are generally added to a dispersion-type aerosol antiperspirant composition to improve adherence of the astringent salt to the skin. This type of formulation is described in many patents, including for example, U.S. Pat. No. 3,968,203, patented Jul. 6, 1976, to Spitzer et al.; U.S. Pat. No. 3,752,540, patented Apr. 13, 1973, to Wahl; U.S. Pat. No. 3,903,258, patented Sep. 2, 1975, to Siegal; and U.S. Pat. No. 3,959,459, patented May 25, 1976, to Curry. These liquids are frequently referred to as nonvolatile oils, as liquid carriers, and as emollients, and the function of the nonvolatile liquid is to adhere the astringent salt to the skin.

The amount of nonvolatile liquid that is employed is selected on the basis of the amount of antiperspirant salt present. The upper limit on the amount used is that which leads to excessive oiliness in the feel of the composition after deposition on the skin.

When a nonvolatile diluent fluid is used in the composition of this invention, the nonvolatile fluid can be present at levels ranging from about 0.5% to about 150% by weight of the antiperspirant salt.

The nonvolatile diluent fluid used in this invention must be miscible with the reinforced silicone gum. Examples of suitable nonvolatile liquids include those disclosed in U.S. Pat. No. 4,152,416 to Spitzer, et al., which is herein incorporated by reference.

Suitable examples include fatty acid esters of polyalkylene glycols wherein the fatty acid contains from about two to about 20 carbon atoms, and from about two to about 200 alkylene glycol units per fatty acid molecule; fatty acid esters of aliphatic alcohols where the esters contain from about 12 to about 26 carbon atoms, such as ethyl laurate, isopropyl myristate, isopropyl palmitate, isopropyl behenate, decyl acetate, behenyl butyrate, hexadecyl acetate, decyl decanoate, methyl oleate, lauryl laurate, oleyl acetate, and dioctyladipate.

Among these various liquid carboxylic acid esters, those having from about 12 to about 26 carbon atoms are preferred. As described above, they can be either aliphatic or aromatic and can contain either one or more ester groups. Especially preferred for use in this invention is isopropyl myristate.

Component C of the composition of this invention is an antiperspirant salt. Any antiperspirant aluminum or zirconium salt can be employed in the antiperspirant compositions of this invention.

Suitable antiperspirant aluminum and/or zirconium salts are any of those well known in the art, whether soluble or insoluble in the antiperspirant compositions of the invention. Generally these are acidic inorganic salts of aluminum and zirconium. Examples of aluminum and zirconium salts are aluminum chlorhydroxide, aluminum chloride, aluminum chlorohydrate, aluminum oxysulfate, zirconyl chloride, zirconyl hydroxychloride, zirconium chlorohydrate, and zirconium oxychloride.

Many inorganic-organic mixtures and complexes are also known antiperspirant salts, such as zirconium salt/amine/and amino acid complexes, Siegel U.S. Pat. No. 3,407,254; zirconium salt/aluminum chlorhydroxide/glycol complexes, Jones et al U.S. Pat. No. 3,405,153; aluminum chlorhydroxide/zirconyl hydroxychloride complexes; and aluminum hydroxide/zirconyl hydroxychloride/amino acid complexes. Also useful are the aluminum and zirconium salts complexed with polyols such as propylene glycol.

In this invention, aluminum chlorohydrate and zirconium chlorohydrate, and mixtures of aluminum chlorohydrate and zirconium chlorohydrate, with or without aluminum chloride or sulfate, are the preferred antiperspirant aluminum and/or zirconium salt. Aluminum chloride and sulfate can also be used, but these are less preferred.

The antiperspirant salt is present in the composition of this invention in an amount within the range from about 2% to about 20% and preferably from about 7% to about 15%.

An aerosol propellant is present in the composition of this invention as component D, which in a gaseous state, carries the other components of the present invention in particulate or droplet form. The aerosol propellants useful in the present invention typically have a boiling point within the range of from about −45° C. to about 5° C. The aerosol propellants are liquefied when packaged in conventional aerosol containers under pressure. The rapid boiling of the aerosol propellant upon leaving the aerosol container aids in the atomization of the other components of the present invention.

Aerosol propellants useful in the present invention include those well known in the art, such as, for example, the chemically-inert hydrocarbons such as propane, n-butane, isobutane and cyclopropane, and mixtures thereof, as well as halogenated hydrocarbons such as dichlorodifluoromethane (propellant 12) 1,1-dichloro-1,1,2,2-tetrafluoroethane (propellant 114), 1-chloro-1,1-difluoro-2,2-trifluoroethane (propellant 115), 1-chloro-1,1-difluoroethylene (propellant 142B), 1,1-difluoroethane (propellant 152A), and monochlorodifluoromethane, and mixtures thereof. Isobutane, used singly or mixed with other hydrocarbons, particularly propane, is preferred for use in the present aerosol antiperspirants. Most preferred are mixtures of isobutane and propane.

Dimethylether in combination with a hydrocarbon propellant such as one of those listed above are also suitable for use in this invention.

Other suitable propellants for use in the present invention include those having the formulas: $CF_3CH_2F$ (designated HFC-134A), $CH_3CHClF$ (designated HCFC-124), $CF_3CHCl_2$ (designated HCFC-123), and $CH_3CCl_2F$ (designated HCFC-141B).

The propellant is present in the composition of this invention in an amount within the range from about 50% to about 90% and preferably about 65% to about 85% by weight of the composition.

In order to prevent caking or settling out of the antiperspirant salt in the compositions of the invention, so that it cannot be dispensed from the aerosol container, a bulking or suspending agent, component E, can be added to the composition of this invention. This is a finely divided particulate material, inert and insoluble in the liquids present, having a particle size below 10 microns in diameter, and includes hydrophobic clays.

Examples of hydrophobic treated clays that swell in organic solvents include hydrophobic bentonite, e.g. Bentone (Registered trademark) 38, and other Bentones, which are bentonite treated with a hydrophobic cationic material such as ditallowalkyldimethylammonium chloride.

When used, the bulking or suspending agent is present in the composition of this invention in an amount from about 0.1% to about 3% and preferably about 0.3% to about 1.5%.

The composition of the present invention may further comprise (F) an alcohol having chainlengths of 1 to about 4 carbon atoms. The alcohol acts as a thickening agent for the bulking agent and as a suspension stabilizing aid.

Examples of suitable alcohols include, for example, methanol, ethanol, isopropanol, butanol, propylene glycol, and glycerol. The most preferred alcohol for use in this invention is ethanol.

Denatured alcohols may also be used in the composition of this invention. Examples of suitable denatured alcohols are disclosed in "CFTA Cosmetic Ingredient Dictionary", Third Edition, pages 276-277, which is herein incorporated by reference. Examples of suitable denatured alcohols include, for example, SD Alcohol 40 (ethyl alcohol denatured with brucine, brucine sulfate, or quassin, and t-butyl alcohol; or denaturing grade denatonium benzoate and t-butyl alcohol in accordance with 27CFR 212.57), SD Alcohol 40-A (ethyl alcohol denatured with t-butyl alcohol and sucrose octaacetate in accordance with 27CFR212.58), and SD Alcohol 40-B (ethyl alcohol denatured with denatonium benzoate and t-butyl alcohol in accordance with 27CFR212.58a). The preferred denatured alcohol for use in this invention is SD Alcohol 40.

When used, the alcohol is generally present in the composition of this invention in an amount within the range of about 0.1% to about 3% and preferably about 0.3% to about 1.5%.

The composition of this invention may also contain other optional components which modify the physical characteristics of the composition or serve as "active" components when deposited on the skin in addition to the antiperspirant material. Additional active components include bacteriostats and fungistats. Non-active components useful herein may include, for example, solvents, emollients, colorants, and perfumes.

The present invention is further directed to a method for preparing the composition of this invention comprising the step of mixing components (A)-(D) and one or more of the optional ingredients described above so as to form a complete and uniform mixture. Generally, high shear mixing of the ingredients with a high speed homogenizer until a homogeneous mixture is formed is preferred. Examples of suitable homogenizers include the Cowles Mixer and the Ross Mixer. The order of mixing the ingredients is not critical; however, in a preferred embodiment of the method of this invention, the reinforced silicone gum is mixed with the diluent of component (B) prior to mixture with the other components of the invention.

The present invention is also directed to a method for reducing the mistiness and dustiness of an aerosol antiperspirant composition upon its dispensation from an aerosol container, comprising the step of uniformly mixing (A) from about 0.1 to about 5.0% of a compound comprising by weight (1) from about 60% to about 95% of a silicone gum and (2) about 5% to about 20% of an untreated reinforcing silica filler or about 5% to about 40% of a treated reinforcing silica filler and (B) from about 3% to about 20% of a diluent fluid selected from a volatile silicone or organic fluid and a mixture of a volatile silicone or organic fluid and a non-volatile silicone or organic fluid with (C) an antiperpirant composition comprising an antiperspirant salt in an amount within the range from about 2 to about 20% and a liquefied propellant in an amount within the range from about 50% to about 90%, the percentages being based on the total weight of the mixture of ingredients. In preferred embodiments, this method further comprises the mixing of from about 0.1% to about 3% of a bulking agent and from about 0.1% to about 3% of a polar organic solvent with the antiperspirant composition.

In order that the invention may be more fully understood, the following examples are given by way of illustration only.

In the examples below, the reinforced silicone gum was dispersed in cyclomethicone pentamer by using a lab scale dough mixer. The cyclomethicone was added with a drip wise addition until the dispersion ratio was 60% cyclomethicone:40% reinforced silicone gum. This produced a thick, grease-like compound which was then readily dispersible in the aerosol premix antiperspirant compositions described below.

EXAMPLES 1-2 AND CONTROL EXAMPLE A

Three aerosol antiperspirant compositions were prepared having the formulations set forth in Tables 1-3 below.

TABLE 1

(Example 1)

| Component | % by weight |
|---|---|
| Reach (Registered Trade Mark) 101[a] | 10.0 |
| isopropyl myristate | 8.4 |
| SE 6035 reinforced Silicone gum[b] | 2.0 |
| cyclomethicone (D-5)[c] | 3.0 |
| Bentone (Registered Trade Mark) 38 | 0.8 |
| SD Alcohol 40 | 0.8 |

TABLE 1-continued (Example 1)

| Component | % by weight |
|---|---|
| Propellant A-46[d] | 75.0 |

[a] aluminum chlorhydrate antiperspirant active, sold by Reheis Chemical Company
[b] reinforced silicone gum, with a Williams Plasticity of 150 to 250 and containing 77% gum and 23% fumed silica, available from General Electric company and used as a mixture of 40% reinforced silicone gum and 60% cyclomethicone pentamer.
[c] the cyclomethicone pentamer contained in silicone gum mixture; see note b.
[d] mixture of 84% isobutane and 16% propane (by weight of total propellant).

TABLE 2

(Example 2)

| Component | % by weight |
|---|---|
| Reach (Registered Trade Mark) 101 | 10.0 |
| isopropyl myristate | 3.4 |
| SE 6035 reinforced Silicone gum | 4.0 |
| cyclomethicone (D-5) | 6.0 |
| Bentone (Registered Trade Mark) 38 | 0.8 |
| SD Alcohol 40 | 0.8 |
| Propellant A-46 | 75.0 |

TABLE 3

(Control Example A)

| Component | % by weight |
|---|---|
| Reach (Registered Trade Mark) 101 | 10.0 |
| isopropyl myristate | 13.4 |
| SE 6035 reinforced Silicone gum | 0 |
| cyclomethicone (D-5) | 0 |
| Bentone (Registered Trade Mark) 38 | 0.8 |
| SD Alcohol 40 | 0.8 |
| Propellant A-46 | 75.0 |

The hydrophobic bentonite clay Bentone 38, the isopropyl myristate, and the SD Alcohol 40 were mixed to form a dispersion. The dispersion was then mixed with the aluminum chlorohydrate, the reinforced silicone gum and the cyclomethicone. The composition was then filled into an aerosol container followed by the addition under pressure of the propellant.

In the examples, the aerosol cans were equipped with a Precision Valve with body orifice of 0.025 inches VT (part no. 07-3468). Two actuators were used, having orifice openings of 0.020 inch NMBU (part no. 01-6845) and 0.016 inch NMBU (part no. 01-6825), respectively. The latter actuator was to test the formulations under more restricted flow characteristics. Can pressure in all cases was 60 PSIG using Propellant A-46, which is a mixture containing 84% isobutane and 16% propane.

Each formulation was sprayed at a target from a distance of 12 inches and over-spray and spray pattern observed on colored paper. Spray bursts of 5, 10, and 15 seconds were used to insure spray uniformity. The following rating system was used to estimate the reduction in spray mist generated:

0—mistier than control (A)
1—same as control (A)
2—½ misting of control (A)
3—⅓ misting of control (A)
4—¼ misting of control (A)
5—very slight or no misting The results are shown in Table 4 below.

TABLE 4

| Rating Results<br>Examples 1-2 and Control Example A | | |
|---|---|---|
| Example No. | Actuator | Rating |
| 1 | 0.020 | 2-3 |
| 1 | 0.016 | 3-4 |
| 2 | 0.020 | 3-4 |
| 2 | 0.016 | 4-5 |

TABLE 4-continued

The data provided in Table 1 above show that compositions containing a reinforced silicone gum (Examples 1 and 2) are dispensed with lower misting upon application than a composition containing no gum (Control Example A). The data further indicates that the combination of a reinforced gum and a more restricted product flow provides the best results. A slight narrowing of the spray pattern was noted with the highest reinforced gum concentration which is an expected characteristic with the reduction of powder misting observed.

EXAMPLES 3-6 AND CONTROL EXAMPLE 8

Aerosol antiperspirant compositions having the formulations shown in Table 5 below were prepared:

TABLE 5

| Formulations<br>Examples 3-6 and Control Example B | | | | | |
|---|---|---|---|---|---|
| | Example No. (Parts by Weight)* | | | | |
| Ingredients | B | 3 | 4 | 5 | 6 |
| Reach 101 | 10.0 | 10.0 | 10.0 | 10.0 | 10.0 |
| SF 1202 | 13.4 | 12.1 | 12.4 | 11.9 | 12.1 |
| SE 6035 | — | 1.3 | — | — | — |
| Bentone 38 | 0.8 | 0.8 | 0.8 | 0.8 | 0.8 |
| SD Ethanol 40 | 0.8 | 0.8 | 0.8 | 0.8 | 0.8 |
| SE73[a] | — | — | 1.0 | 1.0 | 1.0 |
| fumed silica[b] | — | — | — | — | 0.3 |
| amine fluid[c] | — | — | — | 0.5 | — |

[a]silicone gum, with a viscosity of about 40 million centipoise, available from General Electric Company
[b]CAB-O-SIL MS 7 treated with tetramer
[c]diamino-functional silicone, viscosity of approximately 200 centistokes at 25° C., available from General Electric Company as #176-11256
*These weights add up to 25 parts. The other 75 parts is the A-46 propellant when the aerosol can is filled.

In these examples, the cyclomethicone pentamer, Bentone 38 bentonite clay, and, if applicable, the reinforced silicon gum, non-reinforced silicone gum, and amine fluid were mixed in a high speed mixer until a homogenous mixture was formed. The SD Ethanol 40 was added to the mixture, and the resulting mixture was agitated for about 5-10 minutes. The aluminum chlorohydrate and fumed silica (if applicable) were then added and the resulting mixture was mixed for 10-15 minutes or longer if necessary until homogeneous. The mixture was then homogenized for about 3 minutes at high speed.

Control sample B showed typical separation after 24 hours but easily mixed together. Due to the addition of the fumed silica, the composition formed in Example 6 was very difficult to homogenize and was thick and looked grainy after homogenization.

The aerosol cans used to contain the formulations were equipped with a Precision Valve with body orifice of 0.025 inches. Two actuators were used of 0.020 inch NMBU and 0.016 inch NMBU orifice openings. Can pressure in all cases was 60 PSIG using Propellant A-46.

Each formulation was sprayed at a target from a distance of 12 inches and over-spray and spray pattern observed on clear glass with black paper background.

Spray bursts of 5 seconds were used. The following rating system was used:
- 0—mistier than control (B)
- 1—same as control (B)
- 2—¾ misting of control (B)
- 3—½ misting of control (B)
- 4—¼ misting of control (B)
- 5—very slight or no misting The results of Examples 3-6 and Control Example B are shown in Table 6 below.

TABLE 6

Rating Results Examples 3-6 and Control Example B

| Example No. | Actuator | Rating |
|---|---|---|
| (B) | 0.020 | — |
| (B) | 0.016 | — |
| (3) | 0.020 | 5 |
| (3) | 0.016 | 5 |
| (4) | 0.020 | 4 |
| (4) | 0.016 | 4 |
| (5) | 0.020 | * |
| (5) | 0.016 | * |
| (6) | 0.020 | ** |
| (6) | 0.016 | clogged |

\* unable to rate: sprayed a stream - no mechanical break-up
\*\* unable to rate: sprayed a semi-stream to the size of a quarter Each can used in Examples 3-6 and Control Example B was then sprayed to total discharge at 15 second bursts to observe any change in spray characteristics. The results are shown in Table 7 below.

TABLE 7

| Example No. | Actuator | Rating |
|---|---|---|
| (3) | 0.020 | little or no change; no clogging |
| (3) | 0.016 | little or no change until 10% of composition in can was left at which less mechanical breakup occurred, producing a narrower stream |
| (4) | 0.020 | little or no change; no clogging |
| (4) | 0.016 | little or no change until 10% of composition in can was left at which less mechanical breakup occurred, producing a narrower stream |
| (5) | 0.020 | continued as stream - last ¼ of composition in can produced narrower stream |
| (5) | 0.016 | continued as stream; last ¼ of composition in can produced narrower stream; some spitting occurred during discharge |
| (6) | 0.020 | can clogged after ¼ to ⅓ of composition was left. Cleared and then sputtered. |
| (6) | 0.016 | * |

\* - unable to rate

EXAMPLE 7-9

The compositions prepared in Examples 3, 4, and 5 above, respectively, were mixed 50/50 with the composition of control Example B to basically reduce levels of additives by ½. The same basic aerosol packaging was done as in Examples 3-5 except that only a 0.020 actuator was tested. The same spray procedure and evaluation criteria as used in Examples 3-5 were used in Examples 7-9. The results are presented in Table 8 below.

TABLE 8

Rating Results Examples 7-9

| Example No. | Rating |
|---|---|
| (7) | 4-5 |
| (8) | 4 |
| (9) | *** |

\*\*\* Semi-stream -less narrow spray than spray of Example 5 but still unable to rate.

Examples 1-9 and Control Examples A and B show that the presence of a reinforced silicone gum dispersed in a volatile silicone fluid in the aerosol composition provides better anti-misting properties than the presence of a non-reinforced silicone gum. The examples also indicate that poor results are obtained with a composition wherein fumed silica was physically dispersed into the aerosol composition.

What is claimed is:

1. An aerosol antiperspirant composition comprising by weight:
   (A) from about 0.1 to about 5.0% of a compound comprising by weight (1) from about 60% to about 95% of a silicone gum having the following formula:

$[R_a SiO_{(4-a)/2}]_b$ in which R independently represents an unsubstituted or halogenated monovalent hydrocarbon radical having 1 to about 10 carbon atoms, a is a number of from 0 to about 3, and b is a number from about 2000 to about 15,000 and (2) about 5% to about 20% of an untreated reinforcing silica filler which has not been treated to render it essentially hydrophobic or about 5% to about 40% of a treated reinforcing silica filler which has been surface treated so as to render it essentially hydrophobic;
   (B) from about 3% to about 20% of a diluent fluid selected from the group consisting of a volatile silicone, a volatile organic fluid, a mixture of a volatile organic fluid and a non-volatile silicone fluid; and a mixture of a volatile silicone fluid and a non-volatile silicone fluid, wherein the volatile organic fluid is selected from the group consisting of linear hydrocarbons having from about 6 to about 16 carbon atoms and branched isoparaffinic hydrocarbons having from about 6 to about 16 carbon atoms and the non-volatile organic fluid is selected from the group consisting of fatty acid esters of polyalkylene glycols containing from about 2 to about 200 alkylene glycol units per fatty acid molecule wherein the fatty acid contains from about 2 to about 20 carbon atoms and fatty acid esters of aliphatic alcohols wherein the esters contain from about 12 to about 26 carbon atoms;
   (C) an antiperspirant salt in an amount within the range from about 2 to about 20%; and
   (D) a liquefied propellant in an amount within the range from about 50% to about 90%.

2. The composition of claim 1 wherein the compound of component (A) is present in an amount within the range from about 0.5 to about 1.5% by weight.

3. The composition of claim 1 wherein component (A)(2) is a treated reinforcing silica filler.

4. The composition of claim 3 wherein the treated reinforcing silica filler is present in an amount within the range of about 15% to about 30%.

5. The composition of claim 1 wherein component (A)(2) is an untreated reinforcing silica filler.

6. The composition of claim 5 wherein the untreated reinforcing silica filler is present in an amount within the range of about 10% to about 15%.

7. The composition of claim 1 wherein component (A)(2) is a fumed silica or a precipitated silica.

8. The composition of claim 7 wherein component (A)(2) is a fumed silica.

9. The composition of claim 1 wherein in component (A), the silicone gum is an organopolysiloxane having a viscosity of from about 500,000 to about 100,000,000 centistokes at 250° C. having the formula:

$$[R_a SiO_{(4-a)/2}]_b \qquad (I)$$

in which R independently represents an unsubstituted or halogenated monovalent hydrocarbon radicals having 1 to about 10 carbon atoms, and "a" is a number of from 0 to about 3, and "b" is a number from about 2000 to about 15,000.

10. The composition of claim 9 wherein the organopolysiloxane is a linear or branched polydimethylsiloxane blocked with terminal hydroxyl groups, triorganosilyl groups. diorganovinylsilyl groups, organodivinylsilyl groups, or trivinylsilyl groups.

11. The composition of claim 10 wherein the organopolysiloxane is a linear polydimethylsiloxane blocked with terminal dimethylvinylsilyl groups or a linear polydimethylsiloxane blocked with terminal trimethylsilyl groups.

12. The composition of claim I wherein the component B is a volatile silicone fluid.

13. The composition of claim I wherein component B is a mixture of a volatile silicone fluid and a non-volatile organic fluid.

14. The composition of claim 1 wherein the volatile silicone fluid is a volatile cyclic silicone having the formula

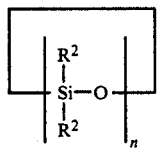

wherein $R^2$ is an alkyl group having 1 to 3 carbons and n is a number from 3 to 10.

15. The composition of claim 14 wherein the volatile cyclic silicone is a cyclomethicone tetramer or a cyclomethicone pentamer.

16. The composition of claim 15 wherein the volatile cyclic silicone is a cyclomethicone pentamer.

17. The composition of claim 1 wherein the nonvolatile fluid is a carboxylic acid ester of an alcohol, the ester having from about 12 to about 26 carbon atoms.

18. The composition of claim 17 wherein the ester is isopropyl myristate.

19. The composition of claim 1 wherein the antiperspirant salt is an aluminum salt, a zirconium salt, or a mixture of an aluminum salt and a zirconium salt.

20. The composition of claim 19 wherein the antiperspirant salt is an aluminum chlorohydrate, a zirconium chlorohydrate or a mixture of an aluminum chlorohydrate and a zirconium chlorohydrate.

21. The composition of claim 1 wherein the propellant is a hydrocarbon propellant.

22. The composition of claim 21 wherein the propellant is a mixture of isobutane and propane.

23. The composition of claim 1 further comprising about 0.1% to about 3% of a bulking agent.

24. The composition of claim 23 wherein the bulking agent comprises a hydrophobic clay having a particle size below 10 microns in diameter.

25. The composition of claim 1 further comprising (F) from about 0.1% to about 3% by weight of an alcohol having from 1 to about 4 carbon atoms.

26. The composition of claim 25 wherein the alcohol is ethanol.

27. The composition of claim 25 wherein the alcohol is a denatured ethanol.

28. A method for preparing an aerosol antiperspirant composition capable of being dispensed from aerosol containers with reduced mistiness and dustiness, comprising the step of mixing to form a homogeneous composition a mixture of ingredients comprising by weight:
(A) from about 0.1 to about 5.0% of a compound comprising by weight (1) from about 60% to about 95% of a silicone gum having the following formula:

$$(R_a SiO(4-a)/2)b$$

in which R independently represents an unsubstituted or halogenated monovalent hydrocarbon radical having 1 to about 10 carbon atoms, a is a number of from 0 to about 3, and b is a number from about 2000 to about 15,000 and (2) about 5% to about 20% of an untreated reinforcing silica filler which has not been treated to render it essentially hydrophobic or about 5% to about 40% of a treated reinforcing silica filler which has been surface treated so as to render it essentially hydrophobic and
(B) from about 3% to about 20% of a diluent fluid selected from the group consisting of a volatile silicone fluid, a volatile organic fluid, a mixture of a volatile silicone fluid and a non-volatile organic fluid, a mixture of a volatile organic fluid and a non-volatile silicon fluid, a mixture of a volatile organic fluid and a non-volatile organic fluid and a mixture of a volatile silicone fluid and a non-volatile silicone fluid wherein the volatile silicone fluid is selected from the group consisting of linear hydrocarbons having from about 6 to about 16 carbon atoms and branched isoparaffinic hydrocarbons having from about 6 to 16 carbon atoms and the non-volatile organic fluid is selected from the group consisting of fatty acid esters of polyalkylene glycols containing from about 2 to about 200 alkylene glycol units per fatty acid molecule wherein the fatty acid contains from about 2 to about 20 carbon atoms and fatty acid esters of aliphatic alcohols wherein the esters contain from about 12 to about 26 carbon atoms with
(C) an antiperspirant salt in an amount within the range from about 2% to about 20%; and
(D) liquefied propellant in an amount within the range from about 50% to about 90%

29. The method of claim 28 wherein the mixture of ingredients further comprises about 0.1% to about 3% of a bulking agent and about 0.1% to about 3% of a polar organic solvent added to the antiperspirant composition.

30. A method for reducing the mistiness and dustiness of an aerosol antiperspirant composition upon its dispensation from an aerosol container, comprising the step of uniformly mixing (A) from about 0.1 to about 5.0% of a compound comprising by weight (1) from about 60% to about 95% of a silicone gum having the following formula:

$$(R_aSiO_{4-a)/2})_b$$

in which R independently represents an unsubstituted or halogenated monovalent hydrocarbon radical having 1 to about 10 carbon atoms, a is a number of from 0 to about 3, and b is a number from about 2000 to about 15,000 and (2) about 5% to about 20% of an untreated reinforcing silica filler which has not been treated to render it essentially hydrophobic or about 5% to about 40% of a treated reinforcing silica filler which has been surface treated so as to render it essentially hydrophobic and (B) from about 3% to about 20% of a diluent fluid selected from the group consisting of a volatile silicone fluid, a volatile organic fluid, a mixture of a volatile organic fluid and a non-volatile organic fluid, a mixture of a volatile organic fluid and a non-volatile silicone fluid, a mixture of a volatile organic fluid and a non-volatile organic fluid and a mixture of a volatile silicone fluid and a non-volatile silicone fluid wherein the volatile organic fluid is selected from the group consisting of linear hydrocarbons having from about 6 to about 16 carbon atoms and branched isoparaffinic hydrocarbons having from about 6 to about 16 carbon atoms and the non-volatile organic fluid is selected from the group consisting of fatty acid esters of polyalkylene glycols containing from about 2 to about 200 alkylene glycol units per fatty acid molecule wherein the fatty acid contains from about 2 to about 20 carbon atoms and fatty acid esters of aliphatic alcohols wherein the esters contain from about 12 to about 26 carbon atoms with (C) an antiperspirant composition comprising an antiperspirant salt in an amount within the range from about 2% to to about 20% and a liquefied propellant in an amount within the range from about 50% to about 90%, the percentages being based on the total weight of the mixture of ingredients.

31. The method of claim 1 further comprising mixing about 0.1% to about 3% of a bulking agent and about 0.1% to about 3% of a polar organic solvent with the antiperspirant composition.

* * * * *